(12) United States Patent
Ibarra et al.

(10) Patent No.: US 7,288,239 B2
(45) Date of Patent: Oct. 30, 2007

(54) METHOD FOR PRODUCING ALKALINE EARTH SULPHATE NANOPARTICLES

(75) Inventors: Fernando Ibarra, Hamburg (DE); Christiane Meyer, Hamburg (DE); Stephan Haubold, Bonn (DE); Thorsten Heidelberg, Hamburg (DE)

(73) Assignee: Nanosolutions GmbH, Hamberg (DE)

( * ) Notice: Subject to any disclaimer, the term of this patent is extended or adjusted under 35 U.S.C. 154(b) by 0 days.

(21) Appl. No.: 10/535,864

(22) PCT Filed: Nov. 19, 2003

(86) PCT No.: PCT/DE03/03823

§ 371 (c)(1),
(2), (4) Date: Sep. 14, 2005

(87) PCT Pub. No.: WO2004/046035

PCT Pub. Date: Jun. 3, 2004

(65) Prior Publication Data

US 2006/0133987 A1 Jun. 22, 2006

(30) Foreign Application Priority Data

Nov. 21, 2002 (DE) ................. 102 54 567

(51) Int. Cl.
- *C01B 17/96* (2006.01)
- *C01F 5/40* (2006.01)
- *C01F 11/46* (2006.01)

(52) U.S. Cl. .............. 423/554; 423/263; 423/544; 423/155; 423/158; 423/161; 423/166; 423/555; 977/773; 977/775

(58) Field of Classification Search ............... 423/263, 423/544, 155, 158, 161, 166, 554, 555; 977/773, 977/775
See application file for complete search history.

(56) References Cited

U.S. PATENT DOCUMENTS

| | | | |
|---|---|---|---|
| 4,894,093 A | 1/1990 | Aderhold et al. | |
| 5,580,377 A * | 12/1996 | Ohtsu et al. | 106/461 |
| 5,698,483 A * | 12/1997 | Ong et al. | 501/12 |
| 6,964,994 B1 | 11/2005 | Antonietti et al. | |
| 2003/0124048 A1 | 7/2003 | Hardinghaus et al. | |
| 2003/0159622 A1 | 8/2003 | Amirzadeh-Asl et al. | |
| 2005/0180912 A1* | 8/2005 | Amirzadeh-Asl et al. | 423/554 |

FOREIGN PATENT DOCUMENTS

| | | |
|---|---|---|
| DE | 37 03 377 A1 * | 8/1988 |
| DE | 37 18 277 A1 | 12/1988 |
| DE | 38 10 423 A1 | 10/1989 |
| DE | 199 34 517 A1 * | 1/2001 |
| DE | 100 05 685 A1 | 8/2001 |
| DE | 100 26 791 A1 * | 12/2001 |
| EP | 0 354 609 A1 * | 2/1990 |
| JP | 4-372712 A * | 12/1992 |
| JP | 06 092630 | 4/1994 |
| JP | 6-92630 A * | 4/1994 |
| WO | WO 01/07487 A1 | 2/2001 |
| WO | WO 01/58809 A2 * | 8/2001 |

OTHER PUBLICATIONS

Gareth D. Rees et al. "Formation and Morphology of Calcium Sulfate Nanoparticles and Nanowires in Water-in-Oil Microemulsions" Langmuir 1999, (15) pp. 1993-2002.*
Mark Summers "Formation of BaSO4 Nanoparticles in Microemulsions with Polymerized Surfactant Shells" Langmuir 2002, (18) pp. 5023-5026.*
Abstract of Japanese Patent Publication No. 2001 048533A, published Feb. 20, 2001.

* cited by examiner

*Primary Examiner*—Timothy C. Vanoy
(74) *Attorney, Agent, or Firm*—Scully, Scott, Murphy & Presser, P.C.

(57) ABSTRACT

The invention relates to synthesis of nanoparticles, in particular to methods for producing nanoparticles with networks consisting of Z sulphate (Z=magnesium (Mg), calcium (Ca), strontium (Sr), barium (Ba) or the binary mixtures thereof). The inventive method consists in synthesising the nanoparticles by crystal growth from an ion Z source and a sulphate ion source in a liquid phase mixture. The invention produces Z sulphate nanoparticles having a small diameter and uniformly dispersible in water or other solvents in a simple way. Co-ordinating solvents like glycerine, glycol ethylene and other polyethylene glycols, polyalcohols or dimethylsulphoxide (DMSO) are used for the synthesis mixture.

15 Claims, 1 Drawing Sheet

METHOD FOR PRODUCING ALKALINE EARTH SULPHATE NANOPARTICLES

PRIOR ART

The present invention relates to the synthesis of nanoparticles. It relates in particular to methods for producing nanoparticles with a lattice essentially consisting of Z sulphate (Z=magnesium (Mg), calcium (Ca), strontium (Sr), barium (Ba) or binary mixtures thereof), in which nanoparticles are synthesised by crystal growth from a Z ion source and a sulphate ion source in a liquid phase synthesis mixture.

Conventional methods for producing Z sulphate ($ZSO_4$) particles are usually carried out as precipitation reactions in an aqueous solution. The resulting size of the primary particles ranges from approximately 100 nanometres to sizes in the millimetre range. Due to the production method, these particles are agglomerated and are not homogeneously dispersible in every desired matrix.

$ZSO_4$ is a known host lattice for dopants and is used in the phosphor industry. It is furthermore an important filling material in the plastics industry. Particle agglomerates produced to date are so large that they clearly modify the optical properties, e.g. the transparency, of the plastic and cannot be incorporated in the polymer matrix in a trouble-free manner. These problems can be avoided with homogeneously distributed nanoparticles whose surface is adapted to the respective matrix. In particular $BaSo_4$ can also be used as a contrast agent for x-ray analysis.

DE 100 05 685 discloses a method for producing barium sulphate nanoparticles having an average particle diameter d50 of 100 to 10,000 nanometres. The particles are produced in an aqueous solution, preferably in a solution containing sodium sulphate ($Na_2SO_4$) or sulphuric acid ($H_2SO_4$).

A disadvantage of this method is that particles having a lower average particle diameter cannot be produced without subjecting them to at least one further method step, namely a milling process (wet milling process).

A further disadvantage is that the synthesised particles are not freely dispersible in water immediately after precipitation out of their synthesis mixture. In order to achieve dispersibility in water, it is suggested in DE 100 05 685 to apply an organic additive to the surface of the particles in a further method step. Three alternatives for this further method step are disclosed, in which:

A) the separated barium sulphate filter cake is first of all processed to form a paste which is then mixed with the additive, or B) the filter cake is suspended in water and the suspension is mixed with the additive, or C) the filter cake is dried and then mixed with the additive, whereby this can preferably occur in a spray milling process in which the additive, if it is present in solid form as the initial substance, first of all has to be made into a solution.

This production method is laborious owing to the subsequent method step for applying the additive and does not render a satisfactory yield, owing at least to the subsequent milling process.

The object of the present invention is therefore to produce at least barium sulphate nanoparticles having a considerably lower average particle diameter in a simple manner, the particles being homogeneously dispersible in water.

ADVANTAGE OF THE INVENTION

The subject matter of the independent claims solves this object not only for barium sulphate nanoparticles, but also for other alkaline earth sulphate nanoparticles, namely magnesium, calcium and strontium sulphate nanoparticles, or for nanoparticles of binary mixtures of the same.

Disclosed according to the invention is a method for producing nanoparticles with a lattice consisting essentially of alkaline earth sulphate, i.e. "Z sulphate" (Z=magnesium (Mg), calcium (Ca), strontium (Sr) or barium (Ba)—or of binary mixtures thereof in any mixing ratio), in which nanoparticles are synthesised by crystal growth from a Z ion source and a sulphate ion source in a liquid phase synthesis mixture, characterised in that the synthesis mixture contains a non-aqueous solvent with coordinating properties which serves as a control component for particle growth.

The particles resulting from the synthesis have a size of 0.5 to 50 nanometres (nm), preferably 2 to 30 nm and particularly preferred 5 to 20 nm, with a size distribution of 50%, preferably 20%, particularly preferred 10 to 15%.

Depending on the selected reaction temperature, reaction time or reactant concentration, particles of different sizes can be obtained specific to recipes. The size distribution is dependant in particular on the molecule used to control growth and on the solvent used. A central function of the coordinating solvent is thereby to slow down crystal growth as compared to synthesis without a coordinating solvent such that it is basically possible, as far as laboratories are concerned, to also introduce the factor of time, in the form of the dwelling time of the nanoparticles in the synthesis mixture, as a control parameter in addition to the aforementioned recipe-specific parameters for controlling growth.

In short, coordinating solvents such as glycerin, ethylene glycol and other polyethylene glycols, polyalcohols or dimethyl sulfoxide (DMSO) are used in the present invention. In addition, the barium is preferably provided as a chloride and the sulphate source as a tetrabutylammonium hydrogen sulphate. Further metal dopants that can be optionally incorporated in the lattice of the nanoparticles during synthesis are also preferably used as chlorides.

In comparison to the prior art, the nanoparticles obtained according to the invention can be produced in an extremely small manner with an average diameter of between 2 and 50 nanometres and can be homogeneously dispersed in water in a particularly preferred manner without any further after-treatment. This is a considerable advantage over the method of the prior art as cited at the beginning hereof since considerable effort is required therein to reduce the size (to a maximum of 100 nanometers) of particles that have formed too large agglomerates (micrometer diameter) during synthesis by means of wet milling. Furthermore, they can also disperse well in many other solvents, if necessary also following an after-treatment. Cited as examples are toluene and chloroform.

Advantageous developments and improvements of the respective subject matter of the invention can be found in the sub-claims.

The synthesis mixture can furthermore also contain a non-coordinating solvent. The particle size can be adjusted depending on its proportion in the entire solvent. The following is basically true: the less coordinating solvent used, the larger the particles.

If most of the solvent of the synthesis mixture has coordinating properties, nanoparticles having an average diameter of less than 50 nm can be produced in many cases.

Advantageous, or more precisely expedient, is the choice of the following initial substances:

as the Z source, $ZCl_2 * 2H_2O$, $ZBr_2 * 2H_2O$, $ZI_2 * 2H_2O$ or $Z(OH)_2$, as the sulphate source, tetrabutylammonium hydrogen sulphate, bis(trimethylsilyl) sulphate, ammonium hydrogen sulphates of the type $R_1R_2R_3R_4NHSO_4$, ammonium hydrogen sulphate, ammonium sulphate, alkali sulphates, alkali hydrogen sulphates, amantadine sulphate, ethylenediammonium sulphate and hydrazinium sulphate, and as the dopant source, the respective metal nitrate, metal bromide or metal iodide, preferably the metal chloride.

The preferably useable dopant is one of the following ions:

Eu(II), Sn(II), Mn(II), Sb(III), Pb(II), Zn(II), Ti(II), V(II), Cu(II), Cd(II), Ce(III), Sm(III), Pr(III), Nd(III), Gd(III), Tb(III), Dy(III), Ho(III), Er(III), Tm(III), Yb(III), Lu(III), Eu(III), Bi(III), Ag(I), Cu(I), or any combination thereof, preferably the combination XY, wherein X=Eu(II), Sn(II), Mn(II), Sb(III), Pb(II), Zn(II), Ti(II), V(II), Cu(II), Cd(II), and Y=Ce(III), Sm(III), Pr(III), Nd(III), Gd(III), Tb(III), Dy(III), Ho(III), Er(III), Tm(III), Yb(III), Lu(III), Eu(III), Bi(III), Ag(I), Cu(I).

An after-treatment of the synthesised nanoparticles which have thus reached their desired size can be optionally and advantageously carried out in order to specifically modify the surface of the nanoparticles depending on their later purpose, and thus to make them suitable therefor. The particles are thereby processed by means of a subsequent chemical modification of the surface such that they can disperse homogeneously in any desired matrix.

As the modification molecule for the nanoparticle surface, for example, a phosphate, preferably trisethyhexyl phosphate or tributyl phosphate, an amine, preferably dodecylamine, a phosphonate, a phosphine, preferably trioctylphosphine, a phosphine oxide, preferably trioctylphosphine oxide, a carboxylic acid, alcohols, preferably polyvalent alcohols, organic esters, silanes, siloxanes, organic sulfones having the formula $RSO_2R$, organic ketones (R—(C=O)—R), organic nitriles. (RCN), organic sulfoxides ($R_2$—$SO_2$), organic amides (R—(C=O)—NR'R or R—(SO)—ONR'R), or perfluorinated modifications of the aforementioned substances, preferably perfluorinated alcohols and possibly related substances, can be specifically selected and used as the modification molecule in order to make the surface-modified nanoparticles homogeneously and finely dispersible in a corresponding matrix, such as silicone oils, teflons, plastics, lacquers, paints, etc, which is then selected similar to that of the modification molecule.

The nanoparticles presented here can now be intravenously applied owing to their small size achieved according to the invention since they are homogeneously distributed and a blocking of veins, arteries and other blood vessels is not to be expected. If the barium sulphate nanoparticles are doped with paramagnetic or radioactive elements, they can be used as a universal carrier for in-vivo diagnostics.

DESCRIPTION OF THE EMBODIMENTS

Figure 1:
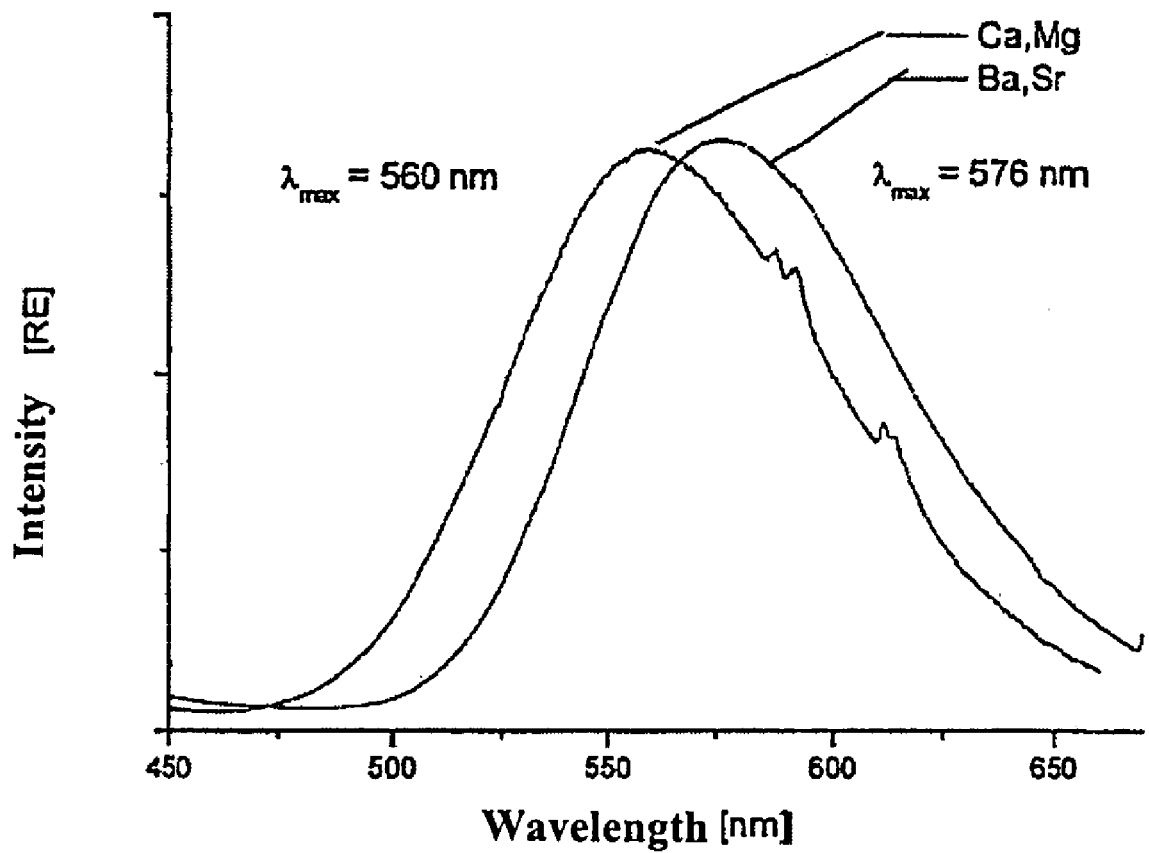
FIG. 1 shows the manganese emission in binary alkaline earth sulphate host lattices ($MSO_4$: Eu, Mn).

The initial substances used are commercially available from the following supply sources:

SIGMA ALDRICH Chemie GmbH, Deisenhofen, Germany,

MERCK, Darmstadt, Germany and

STREM, Karlsruhe, Germany.

Embodiment Examples

1.

55 g of $BaCl_2$ are weighed out into a round-bottomed flask and are dissolved in 300 ml of glycerin. 30 g of imidazole dissolved in glycerin are then added to the Ba-containing solution and the reaction mixture is subsequently dried by gentle heating for 24 hours. In parallel, 73 g of tetrabutylammonium hydrogen sulphate are dissolved in glycerin and are dried over night. Both solutions are then mixed together at 70° C. and stirred for one hour. Following the addition of 0.5 equivalents of water based on glycerin, the thus synthesised barium sulphate particles are washed with isopropanol precipitated with ethanol and are subsequently dried. Approximately 60 g of barium sulphate nanoparticles having a homogeneous size distribution of 22% around an average particle size of 19 nm are produced.

2.

A small amount of 1 g of $BaCl_2$ and 0.15 g of $MnCl_2$ is dissolved in ethylene glycol and is dried overnight at 50° C. 0.07 g of $EuCl_3$, 0.54 g of imidazole and 1.32 g of tetrabutylammonium hydrogen sulphate are dissolved in a second vessel and are dried at room temperature (RT) overnight. Both solutions are subsequently mixed at RT and are then stirred at 180° C. for two hours. The resulting precipitate is centrifuged off and washed with methanol. Approximately 1 g of $BaSO_4$: Mn, Eu nanoparticles having a homogeneous size distribution of 15% around an average particle size of 10 nm is produced. In an advantageous manner $EuCl_3$ (EuCl sub3) is used as the initial substance in order to incorporate Eu(II) as ions in the lattice. This is much cheaper and enables a simpler and more successful synthesis than if $EuCl_2$ (EuCl sub2) were to be used as the initial substance. The method can also be carried out for larger amounts according to the described method.

3.

0.92 g of $BaCl_2$ and 0.54 g of imidazole are dissolved in a 1:1 mixture of water and methanol in a round-bottomed flask. Following the addition of 25 ml of dimethyl sulfoxide (DMSO), the water and methanol are distilled off at RT and under vacuum. 0.044 g. of $Eu(II)Cl_2$ and 1.32 g of tetrabutylammonium hydrogen sulphate in DMSO are then added one after the other. The reaction mixture is then stirred for 0.5 hours at 170° C. Approximately 1 g of $BaSO_4$: Eu++ nanoparticles having a homogeneous size distribution of 20% around an average particle size of 10 nm was obtained.

The method can also be carried out for larger amounts according to the described method.

4. After-Treatment:

Barium sulphate, produced in the manner described above in 1, is mixed in a sufficient amount with dodecylamine as the modification molecule—at least in the ratio of 1:1% by weight of barium sulphate to modification molecule—and is then heated, preferably with the exclusion of oxygen, to the boiling temperature of the dodecylamine, preferably 100 to 300° C., and is kept there for 0.1 to 2 hours whilst being stirred constantly. This results in the solubility of the nanoparticles in toluene.

5.
Binary mixture of magnesium/calcium: Mg, CaSO$_4$: Eu(II), Mn(II)

0.305 g of MgCl$_2$, 0.329 g of CaCl$_2$ and 0.158 g of MnCl$_2$ are stirred in 25 ml of ethylene glycol at room temperature (RT) until the metal salts have completely dissolved and are subsequently dried overnight under vacuum at 50° C.

At the same time, 0.0446 g of EuCl$_2$ are dissolved in 3 ml ethylene glycol, 0.5446 g are dissolved in 3 ml of ethylene glycol and 1.3242 g of tetrabutylammonium hydrogen sulphate are dissolved in 10 ml of ethylene glycol and are dried overnight at RT. Imidazole solution, Eu(II) solution and sulphate solution are then added to the metal salts under nitrogen. The finished reaction mixture is subsequently heated to 180° C. and stirred for two hours. The resulting precipitate is centrifuged off, washed with methanol and then dried. The particle size is 10 to 15 nm and has a size distribution of 10 to 20%.

The method can also be carried out for larger amounts according to the described method. According to the invention, it is possible to profit from a further effect: the addition of magnesium (Mg) causes a shift in the manganese emission and thus a change in the colour impression.

The position of the manganese fluorescence bands is determined by the lattice-forming alkaline earth ion such that shifts of the bands can be caused by binary mixtures. This is accompanied by a change in the colour impression. This effect is shown, as an example, in FIG. 1, wherein a shift in the emission bands by approximately 16 nm occurs, thus shifting the emission maximum from approximately 576 nm to 560 nm.

Further embodiments for the production of calcium sulphate nanoparticles can be seen from the above embodiments by replacing the barium with calcium in a stoichiometrically adjusted ratio.

Further embodiments for the production of strontium sulphate nanoparticles can be seen from the above embodiments by replacing the barium with strontium in a stoichiometrically adjusted ratio.

Further embodiments for the production of magnesium sulphate nanoparticles can be seen from the above embodiments by replacing the barium with magnesium in a stoichiometrically adjusted ratio.

End of the Embodiments.

Uses of the produced nanoparticles:

It should be noted that owing to the present invention, the targeted selection of dopants according to their physical properties, such as paramagnetism and light absorption or emission, enables use of the Z sulphate according to the invention having an average particle size of 0.5 to 50 nm as an intravenously or intramuscularly applicable in vivo diagnostic agent for x-ray analysis, computer tomography analysis, magnetic resonance imaging analysis or for fluorescence analysis in organic systems, particularly for plants. The incorporation of many dopants which are generally toxic as a pure substance is harmless to the human body if these are integrated in the host lattice of the nanoparticles. The extremely small particle size enables marker liquids carrying these nanoparticles to also flow through the narrowest cross-sections, without blocking these.

It is also possible to use the Z sulphate nanoparticles according to the invention having an average particle size of 0.5 to 50 nm as a carrier and host lattice for radioactive isotopes in isotope diagnostics.

The substance Z sulphate produced according to the invention in the form of nanoparticles having an average particle size of 0.5 to 50 nm can advantageously also be used as a filling material for the smallest plastic parts and the thinnest films, with the aim of improving the mechanical behaviour of the plastic without loss of the optical properties, and can furthermore be used for paints and lacquers without influencing the flowability or other properties thereof. They can also be used for products such as car tyres, film bases or as an intermediate product for master batches and compounds.

Even though the present invention was described above by means of a preferred embodiment, it is not limited hereto, but can rather be modified in a number of manners.

Finally, the present invention is not restricted to the simplified production of Z sulphate particles up to 50 nanometres. Considerable advantages can also be achieved with the synthesis of Z sulphate nanoparticles having a particle diameter d50>50 or d50>100 nanometres since the nanoparticles, in contrast to the prior art, are produced in a one step method, which simplifies and reduces the cost of production. For this purpose, the nanoparticles are left in the synthesis mixture for longer.

Finally, the features of the sub-claims can be essentially freely combined with one another and not by the sequence given in the claims, provided that they are independent of one another.

The invention claimed is:

1. Nanoparticles having a crystal lattice or, in the case of doping, a host lattice essentially consisting of Z sulphate (Z=magnesium (Mg), calcium (Ca), strontium (Sr) or barium (Ba)), which can be obtained by synthesis under controlled crystal growth in a non-aqueous solvent with coordinating properties, the nanoparticles having an average particle size of 0.2 to 50 nanometres and the property that they are dispersible in water.

2. A method for producing nanoparticles having a crystal lattice or, in the case of doping, a host lattice essentially consisting of Z sulphate (Z=magnesium (Mg), Z=calcium (Ca), strontium (Sr) or barium (Ba)), in which the nanoparticles are synthesised by crystal growth from a Z ion source and a sulphate ion source in a liquid phase synthesis mixture, characterized in that the synthesis mixture contains a non-aqueous solvent with coordinating properties which acts as a control component for particle growth and characterized in that said nanoparticles have an average particle size of 0.2 to 50 nanometers and are dispersible in water.

3. The method according to claim 2, characterized in that glycerin, ethylene glycol, polyethylene glycols, polyalcohols or dimethyl sulfoxide (DMSO) is used as the non-aqueous solvent with coordinating properties.

4. The method according to claim 3, wherein combinations of the non-aqueous solvent with coordinating properties are used.

5. The method according to claim 2, 3 or 4, wherein to synthesize doped Z sulphate nanoparticles, an alkaline-acting component is added to the synthesis mixture.

6. The method according to claim 5, wherein dimethyl sulfoxide (DMSO) is used as the non-aqueous solvent with coordinating properties for synthesizing manganese- and europium (II)-doped Z sulphate nanoparticles and imidazole is added as alkaline-acting component.

7. The method according to claim 2, wherein the synthesis mixture furthermore contains a non-coordinating solvent.

8. The method according to claim 7, wherein most of the solvent of the synthesis mixture has coordinating properties.

9. The method according to claim 2, wherein one or more of: tetrabutylammonium hydrogen sulphate, bis(trimethylsilyl) sulphate, ammonium hydrogen sulphate, ammonium sulphate, alkali sulphates, alkali hydrogen sulphates, amantadine sulphate, ethylenediammonium sulphate and hyrazinium sulphate is used as the sulphate ion source.

10. The method according to claim 2, further comprising the following after-treatment step:
heating the synthesised nanoparticles in the presence of a modification molecule to modify the surface of said synthesized nanoparticles, wherein the modification molecule is selected from the following group:
a phosphate, an amine, a phosphonate, a phosphine, a phosphine oxide, a carboxylic acid, alcohols, glycerin, ethylene glycol, polyglycols, organic esters, silanes, siloxanes, organic sulfones, organic ketones, organic nitriles, organic sulfoxides, organic amides and perfluorinated modifications of the aforementioned substances.

11. The method according to claim 5, wherein the alkaline-acting component is an amine.

12. The method according to claim 11, wherein the amine is trioctylamine.

13. The method according to claim 5, wherein the alkaline-acting component is imidazole.

14. The nanoparticles, according to claim 1, wherein the non-aqueous solvent with coordinating properties is glycerin, ethylene glycol, polyethylene glycol, polyethylene glycols, polyalcohol or dimethyl sulfoxide (DMSO).

15. The nanoparticles according to claim 14, wherein ethylene glycol is used as the non-aqueous solvent with coordinating properties.

* * * * *